United States Patent
Bolger et al.

(10) Patent No.: US 6,796,985 B2
(45) Date of Patent: Sep. 28, 2004

(54) METHOD FOR DRILLING BONE, IN PARTICULAR FOR SETTING A PEDICLE SCREW, EQUIPMENT, INSTRUMENT AND CONTROL DEVICE FOR IMPLEMENTING SAID METHOD

(75) Inventors: Ciaran Bolger, Bristol (GB); John Bolger, Dublin (IE)

(73) Assignee: Spinevision S.A. (FR)

( * ) Notice: Subject to any disclaimer, the term of this patent is extended or adjusted under 35 U.S.C. 154(b) by 360 days.

(21) Appl. No.: 10/109,276

(22) Filed: Mar. 27, 2002

(65) Prior Publication Data

US 2002/0161372 A1 Oct. 31, 2002

Related U.S. Application Data

(63) Continuation-in-part of application No. 10/019,717, filed on May 15, 2002, now abandoned.

(30) Foreign Application Priority Data

Jul. 1, 1999 (FR) .......................................... 99 08497

(51) Int. Cl.$^7$ ............................................. A61B 17/16
(52) U.S. Cl. ....................................... 606/80; 606/104
(58) Field of Search ............................. 606/79, 80, 86, 606/96, 98, 104

(56) References Cited

U.S. PATENT DOCUMENTS

| | | | |
|---|---|---|---|
| 4,824,433 A | 4/1989 | Marz et al. | |
| 5,196,015 A | 3/1993 | Neubardt | |
| 5,284,153 A | 2/1994 | Raymond et al. | |
| 5,779,642 A | 7/1998 | Nightengale | |

*Primary Examiner*—Brian L. Casler
*Assistant Examiner*—John R Sanders
(74) *Attorney, Agent, or Firm*—Bachman & LaPointe, P.C.

(57) ABSTRACT

The present invention concerns a method and equipment for drilling bone, in particular for setting a pedicle screw using a manual or motorized drilling tool. The equipment includes a drilling instrument, a source of electric impulses and a connector for connecting the electric impulse source to the drilling instrument. The equipment includes at least one sensor for detecting a muscle signal either implanted in a muscle or placed on the skin in the vicinity of a muscle before and during drilling. An alert is produced in the event of detection by at least one sensor of a muscle signal correlated with the source of electric impulses connected to the drilling instrument.

40 Claims, 2 Drawing Sheets

METHOD FOR DRILLING BONE, IN PARTICULAR FOR SETTING A PEDICLE SCREW, EQUIPMENT, INSTRUMENT AND CONTROL DEVICE FOR IMPLEMENTING SAID METHOD

CROSS-REFERENCE TO RELATED APPLICATION(S)

This application is a continuation-in-part of U.S. Ser. No. 10/019,717, filed May 15, 2002 now abandoned, entitled DRILLING METHOD AND INSTRUMENT FOR SETTING A PEDICLE SCREW (Attorney's Docket No. 01-767).

BACKGROUND OF THE INVENTION

The present invention concerns the area of spinal surgery, more precisely the drilling of vertebral pedicles, in particular for setting pedicle screws.

The use of manual or motorized drilling instruments is known, alternatively rotating or mobile around a median position.

In particular European patent EP287823 is known describing a surgical instrument for manual use, especially for osteosynthesis, fitted with a handle to which is attached a tool such as a screwdriver tip or bore, with a shaft having coaxial rotational support within the handle and on which two cogwheels are fixed distant from one another, with a stop pawl arranged in the handle and actuated from outside, and which in one end-stroke position only engages into to the crown wheel of one of the cogwheels, and which at the other end-stroke position only engages into the crown wheel of the other cogwheel.

The problem which arises with the instruments of the state of the art relates to the guiding of the drilling instrument, and more precisely to the choice of entry point and orientation of the drilling tool in order to avoid any risk of going beyond the pedicle.

The difficulty derives from the need to cross through cancellous bone while remaining in contact with cortical bone, it being essential to avoid a pathway that is too lateral which could injure the spinal cord or the spinal nerves.

The difficulty is further increased if the pedicle is deformed requiring the drilling instrument to emerge at one point of the pedicle and to return inside the pedicle beyond the deformation without harming innervated parts.

Clinical trials show that that no satisfactory solution has been found to this problem at the present time, and it would appear that 25% of pedicle screws are ill-positioned.

To meet this problem, the invention consists of detecting a nerve or nerves by electrifying the drilling instrument.

It is true that the prior art contains documents concerning the detection of muscular response by analysis of an electric signal. But the end purpose of such equipment is the monitoring of nerve activity, in particular during anaesthesia.

American patent U.S. Pat. No. 5,284,153, for example, is known. This document discloses and claims a method for locating a nerve. It suggests several steps including the determination of the distance between the nerve and stimulation means. This step is of no interest in bringing an answer to the problem of guiding an instrument for drilling a vertebral pedicle.

American patent U.S. Pat. No. 5,779,642 discloses a method of locating a nerve for guiding a puncture needle, which uses a needle-locating step by means of ultrasound. Patent U.S. Pat. No. 4,824,433 also concerns an application for positioning a puncture needle, through the use of an electric current supplying the needle and the detection of this signal.

Patent U.S. Pat. No. 4,962,766 discloses equipment for locating nerves during surgery. The purpose is the study of nerve function.

None of these documents expressly concerns, nor suggests, the guiding of a drilling instrument for drilling a vertebral pedicle.

American patents U.S. Pat. Nos. 5,196,015 and 5,474,558 are also known, concerning a method for inserting a pedicle screw, according to which the evoked potential is detected at the time of insertion of a pedicle screw. Detection of patient reaction is made by visual observation, which cannot guarantee a sufficiently fast reaction on the part of the surgeon. In addition, the trigger threshold of the reaction is dependent upon the patient, upon patient condition, and cannot guarantee satisfactory reliability and sensitivity in detection.

SUMMARY OF THE INVENTION

The invention, in its more general sense, concerns equipment for drilling bone, in particular for setting a pedicle screw in accordance with claim 1.

The equipment of the invention comprises a drilling instrument, a source of electric impulses and means for connecting the electric impulse source to the drilling instrument. The equipment also comprises at least one sensor for detecting a muscle signal intended to be implanted in a muscle or placed on the skin in the vicinity of a muscle before drilling is started and during drilling, and means to produce an alert in the event of detection by at least one sensor of a muscle signal correlated with the electric impulse source connected to the drilling instrument.

The electric impulses are of fixed frequency and the alert means is triggered whenever the detected signal has identical frequency to the frequency of the electric impulses.

According to one variant, the means of alert is a sound and/or tactile and/or light signal.

According to one particular embodiment, the source of electric impulses connected to the drilling instrument delivers a signal in the form of impulses having a frequency of 5 hertz or less.

According to a first variant, the source of electric impulses is connected to the drilling instrument by means of an electric cord.

In a second variant, the source of electric impulses is positioned inside the drilling instrument.

The sensor or sensors is or are connected to the drilling instrument by means of an electric cord.

The invention also concerns an instrument for drilling bone, in particular for drilling a vertebral pedicle, intended to prepare the pedicle prior to setting a pedicle screw.

According to one particular variant, the means for connecting the drilling instrument to the source of electric impulses is formed of a rotating connector.

The invention also concerns a control device for the bone drilling equipment according to the invention.

According to one particular variant, the control device comprises an output connectable to the drilling tool and a detection circuit whose output is connectable to at least one sensor.

According to another particular variant, the control device is incorporated in a handle of the drilling instrument.

The invention further concerns an assembly made up of two sensors of a particular type, electric sensors, for bone drilling equipment according to the invention in which said sensors are positioned at invariable distance from one another.

The invention further concerns a method for drilling bone, vertebral pedicles in particular, for setting in place a pedicle screw using drilling equipment which comprises:

- a manual or motorized drilling instrument able to drive a drilling tool in rotation,
- a source of electric impulses and means for connecting the electric impulse source to the drilling instrument, and
- at least one sensor to detect a muscle signal intended to be implanted in a muscle or placed on the skin in the vicinity of a muscle and connected to a control device,
- in which said source of electric impulses sends electric impulses into said drilling tool, and in which, throughout drilling, said control device analyses the signal received from at least one detection sensor, and uses an alert-producing means in the event of detection by at least this sensor of a muscle signal correlated with the source of electric impulses connected to the drilling instrument.

According to one preferred embodiment, the entry point or orientation of the drilling instrument is modified in the event that the alert means is triggered.

BRIEF DESCRIPTION OF THE DRAWINGS

The invention will be better understood on reading the following description with reference to the appended drawings in which.

DETAILED DESCRIPTION OF THE PREFERRED EMBODIMENTS

Figure 1:
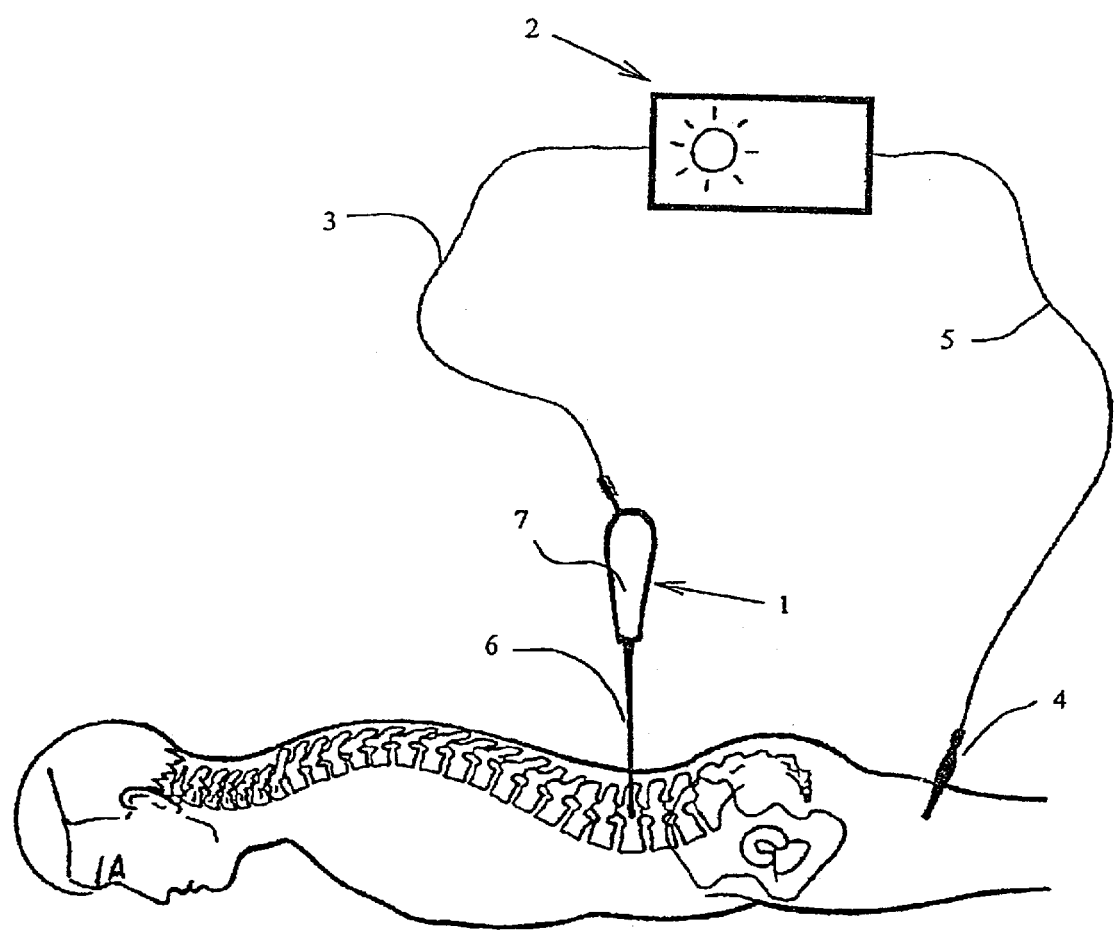
FIG. 1 represents a diagrammatic view of a first variant of equipment according to the invention.

The equipment according to the first variant of embodiment of the invention, illustrated in FIG. 1, comprises a drilling instrument 1 connected to a control box 2 via a sterile electric cord 3. The control box 2 is also connected to a sensor, forming an electrode, formed of a fine needle 4, via another sterile electric cord 5.

The drilling instrument 1 comprises a drill-bit or metal drill forming a drilling tool 6 integral with a handle 7 that is fixed or comprises a motor. The connection between the electric cord 3 and the drilling tool 6 is made by means of a rotating electric connector or chuck in conductor material and a connecting terminal provided on the handle or on the motor unit of the drilling tool.

Control box 2 delivers an electric signal of low current and low voltage. This signal is constant with a frequency of 5 hertz or less, in order to allow the signal detected by the needle 4 to be correlated with the signal applied to the drilling tool 6 and to eliminate interference signals.

The needle 4 is implanted in an appropriate leg muscle of the patient. The electronic circuit of control box 2 comprises a detector synchronous with the generator of electric impulses. The detection by needle 4 of an electric signal by the muscle causes the emission of a sound and/or visual signal, warning the surgeon of contact between the drilling instrument 1 and soft tissue surrounding at least one nerve.

It is also possible to use several needles 4 implanted in pairs in each muscle (electromyography detection).

The alert may be a sound signal, such as a sound of set frequency and/or tactile vibration emitted by a vibrating device and perceived by the operator of the drilling instrument and/or a light emitted by a lamp or an electroluminescent diode.

The alert means is set off whenever the detected signal has an identical frequency to the frequency of the electric impulses emitted by the electric impulse source.

Therefore, correlation is not so much made by the value of the muscle signal detected by the sensor but rather by the frequency of this signal, irrespective of the form of the signal.

For example, it is perfectly feasible to use not an electric impulse sensor, but a movement sensor placed on the skin surrounding the muscle.

Figure 2:
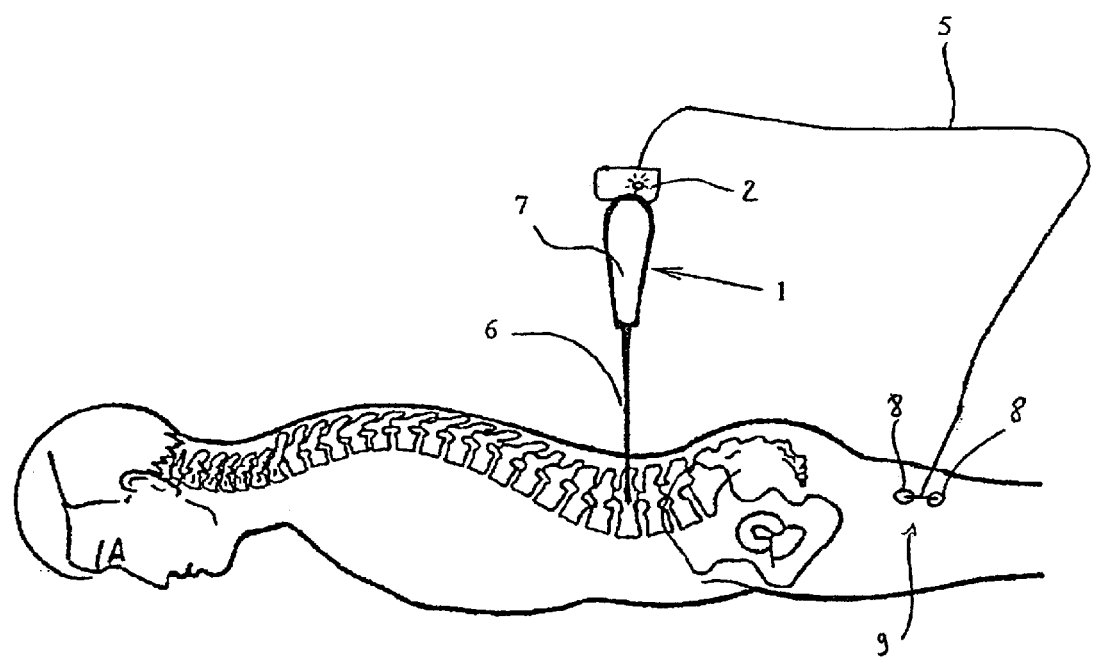
FIG. 2 is a diagrammatic view of a second variant of equipment according to the invention.

Under a second variant of the invention, illustrated in FIG. 2, the control box 2 is incorporated in the handle 7 of the drilling instrument 1, and there is therefore no electric cord between the control box 2 and the drilling instrument 1.

The production of the alert signal by vibration can therefore be made directly in the palm of the operator for example who is holding the handle 7.

It is also possible to use one or several sensors of "patch" type 8 to be positioned on the skin.

The sensors, whether needle or patch, if they are electric are preferably positioned in pairs for each muscle, and each pair forms a sensor assembly 9, as can be seen in FIG. 2, in which the distance between the sensors is fixed and cannot vary. This distance may be optimised in relation to the muscle signal received. The two sensors may therefore, for example, be positioned on a single patch.

When using the drilling equipment of the invention to drill a pedicle, the drilling tool 6 is positioned at an entry point by the operator of the drilling instrument (the surgeon).

Prior to the actual drilling step, the operator positions the sensor or sensors on or in the patient's body.

To test the efficacy of the equipment, the operator may place the drilling tool 6 in contact with the soft tissue surround the entry point. This should trigger the chosen alert means.

Throughout drilling, said control device analyses the signal received from the detection sensor or sensors, and whenever a sensor captures a signal which is correlated with the signal from the electric impulse source connected to the drilling instrument, the control device sets in operation a means producing an alert.

Should an alert means be triggered during drilling, the surgeon may therefore change the orientation of the drilling instrument and possibly withdraw the drilling instrument 1 to engage the drilling tool 6 at a staggered entry point.

After drilling, especially if the alert means has not been triggered during drilling, and to insure that the equipment has functioned properly, the operator may also test the efficacy of the equipment by placing the drilling tool 6 in contact with the soft tissue surrounding the entry point. This should trigger the chosen alert means.

What is claimed is:

1. Equipment for drilling bone for setting a screw using a drilling tool, said equipment comprising a drilling instrument including said drilling tool, a source of electric impulses, means for connecting the electric impulses source to the drilling instrument, at least one sensor for detecting a muscle signal, and means for producing an alert in the event of detection by said at least one sensor of a muscle signal correlated with the source of electric impulses connected to the drilling instrument.

2. Equipment according to claim 1, wherein said at least one sensor is implanted in a muscle before and during drilling.

3. Equipment according to claim 1, wherein said at least one sensor is placed on skin in the vicinity of a muscle before and during drilling.

4. Equipment according to claim 1, wherein said alert producing means produces at least one of a sound, a tactile, and a light signal.

5. Equipment according to claim 1, wherein electric impulses produced by said electric impulses source have a fixed frequency and said alert means is triggered when the detected muscle signal has a frequency identical to the frequency of said electric impulses.

6. Equipment according to claim 1, wherein said electric impulses sources delivers electric impulses having a frequency no greater than 5 Hertz.

7. Equipment according to claim 1, wherein said source of electric impulses is connected to the drilling instrument by means of an electric cord.

8. Equipment according to claim 1, wherein said electric impulses source is positioned inside the drilling instrument.

9. Equipment according to claim 1, wherein the at least one sensor is connected to the drilling instrument by an electric cord.

10. Bone drilling equipment for drilling vertebral pedicles to prepare a setting for a pedicle screw comprising a bone drilling instrument having a drilling tool, a source of electric impulses, means for connecting the electric impulses source to the drilling instrument, at least one muscle signal detection sensor, and means for producing an alert in the event of detection by said at least one muscle signal detection sensor of a muscle signal correlated with the source of electric impulses connected to the drilling instrument.

11. Bone drilling equipment according to claim 10, wherein said at least one muscle signal detection sensor is implanted in a muscle before drilling and during drilling.

12. Bone drilling equipment according to claim 10, wherein said at least one muscle signal detection sensor is placed on skin in the vicinity of a muscle before drilling and during drilling.

13. Bone drilling equipment according to claim 10, wherein said alert producing means produces at least one of a sound, tactile, and light signal.

14. Bone drilling equipment according to claim 10, wherein said electric impulses have a fixed frequency and said alert producing means is triggered when the detected signal has a frequency identical to the frequency of said electric impulses.

15. Bone drilling equipment according to claim 10, wherein the electric impulses source connected to the drilling instrument delivers electric impulses having a frequency no greater than 5 Hertz.

16. Bone drilling equipment according to claim 10, wherein the electric impulses source is connected to the drilling instrument by an electric cord.

17. Bone drilling equipment according to claim 10, wherein the electric impulses source is positioned inside said drilling instrument.

18. Bone drilling equipment according to claim 10, wherein the at least one muscle signal detection sensor is connected to the drilling instrument by an electric cord.

19. Bone drilling equipment according to claim 10, wherein the means for connecting the drilling instrument to the electric impulses source is formed by a rotating connector.

20. Control device for bone drilling equipment using a drilling instrument having a drilling tool, said bone drilling equipment comprising at least one sensor for detecting a muscle signal, said control device comprising a source of electric impulses, means for connecting the electric impulses source to the drilling instrument, and means for producing an alert in the event of detection by said at least one sensor of a muscle signal correlated with the electric impulses source connected to the drilling instrument.

21. Control device according to claim 20, wherein the alert producing means produces at least one of a sound, tactile, and light signal.

22. Control device according to claim 20, wherein the electric impulses have a fixed frequency and the alert producing means is triggered whenever the detected signal has a frequency identical to the frequency of the electric impulses.

23. Control device according to claim 20, wherein the electric impulses source delivers electric impulses having a frequency no greater than 5 Hertz.

24. Control device according to claim 20, wherein the electric impulse source is connected to the drilling instrument by an electric cord.

25. Control device according to claim 20, wherein the electric impulses source is positioned inside the drilling instrument.

26. Control device according to claim 20, wherein the at least one sensor is connected to the drilling instrument by an electric cord.

27. Control device according to claim 20, wherein the control device has an output connectable to the drilling tool and a detection circuit having an output which is connectable to said at least one sensor.

28. Control device according to claim 20, wherein the control device is incorporated in a handle of the drilling instrument.

29. An assembly made up of two electric sensors for bone drilling equipment for drilling vertebral pedicles for setting in place pedicle screws, said drilling equipment comprising a drilling instrument, a source of electric impulses, means for connecting the electric impulses source to the drilling instrument, at least one sensor for detecting a muscle signal and means for producing an alert in the event of detection by said at least one sensor of a muscle signal correlated with the electric impulses source connected to the drilling instrument, and said two electric sensors being positioned at an invariable distance from one another.

30. Method for drilling bone using drilling equipment comprising:

providing a drilling instrument able to drive a drilling tool in rotation;

providing a source of electric impulses and means for connecting the electric impulses source to the drilling instrument;

providing at least one sensor for detecting a muscle signal connected to a control device;

sending electric impulses from said electric impulses source into said drilling tool; and during drilling, analyzing a signal received from said at least one sensor with said control device and setting in operation a means for producing an alert in the event of the detection by the at least one sensor of a muscle signal correlated with the electric impulses source connected to the drilling instrument.

31. A method according to claim 30, further comprising implanting said at least one sensor in a muscle.

32. A method according to claim 30, further comprising placing said at least one sensor on skin in the vicinity of a muscle.

33. A method according to claim 30, further comprising generating at least one of a sound, tactile, and light signal with said alert producing means.

34. A method according to claim 30, further comprising generating electric impulses having a fixed frequency with said electric impulses source and said setting in operation step comprising triggering said alert producing means whenever the detected signal has a frequency identical to the frequency of the electric impulses.

35. A method according to claim 34, wherein said electric impulses generating step comprises generating electric impulses having a frequency no greater than 5 Hertz.

36. A method according to claim 30, further comprising connecting said electric impulses source to said drilling instrument by an electric cord.

37. A method according to claim 30, further comprising positioning said electric impulse source inside the drilling instrument.

38. A method according to claim 30, further comprising connecting the at least one sensor to the drilling instrument by an electric cord.

39. A method according to claim 30, further comprising modifying an entry point of the drilling instrument in the event that the alert producing means is triggered.

40. A method according to claim 30, further comprising modifying an orientation of the drilling instrument in the event that the alert producing means is triggered.

* * * * *